ically acceptable acid-addition salts
United States Patent
Denzel et al.

[11] 4,072,681
[45] Feb. 7, 1978

[54] 3,7-DIHYDRO- AND 1,7-DIHYDRO-4H-PYRAZOLO[4',3':5,6]-PYRIDO[4,3-d]PYRIMIDIN-4-ONES

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 773,562

[22] Filed: Mar. 2, 1977

[51] Int. Cl.² .................. A61K 31/415; C07D 471/14
[52] U.S. Cl. .............................. 260/256.4 F; 424/251
[58] Field of Search .................................. 260/256.4 F

[56] References Cited
U.S. PATENT DOCUMENTS 3,894,021  7/1975  Denzel et al. ................. 260/256.4 F

*Primary Examiner*—Paul M. Coughlan, Jr.
*Assistant Examiner*—James H. Turnipseed

*Attorney, Agent, or Firm*—Lawrence S. Levinson; Merle J. Smith

[57] ABSTRACT

New 3,7-dihydro and 1,7-dihydro-4H-pyrazolo[4',3':5,6]pyrido[4,3-d]pyrimidin-4-ones which have the general formula

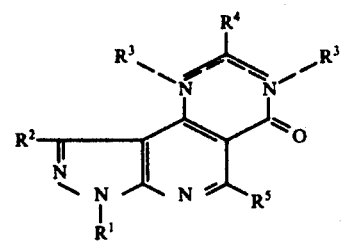

are useful as anti-inflammatory agents and central nervous system depressants.

19 Claims, No Drawings

3,7-DIHYDRO- AND 1,7-DIHYDRO-4H-PYRAZOLO[4',3':5,6]-PYRIDO[4,3-d]PYRIMIDIN-4-ONES

SUMMARY OF THE INVENTION

This invention relates to new 3,7-dihydro and 1,7-dihydro-4H-pyrazolo[4',3':5,6]pyrido[4,3-d]pyrimidin-4-one compounds. These new compounds have the general formula

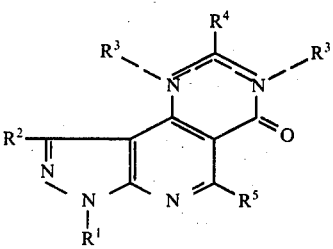
(I)

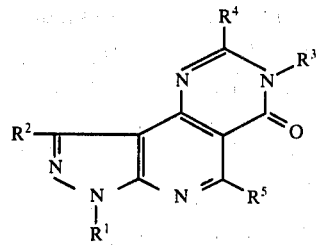
(Ia)

or the double bond is in the 2,3-position and $R^3$ is attached to the nitrogen in the 1-position and the compounds of the invention are 1,7-dihydro-4H-pyrazolo[4',3':5,6]-pyrido[4,3-d]pyrimidin-4-ones which have the formula

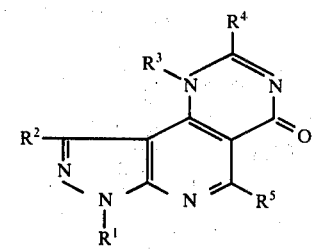
(Ib)

$R^1$ is hydrogen, lower alkyl or phenyl.

$R^2$, $R^4$ and $R^5$ each is hydrogen or lower alkyl.

$R^3$ is hydrogen, lower alkyl, phenyl, substituted phenyl, phenyl-lower alkyl or di(lower alkyl)amino-lower alkyl.

The lower alkyl groups are straight or branched chain hydrocarbon radicals of up to seven carbons like methyl, ethyl, propyl, isopropyl, butyl, isobutyl, t-butyl and the like. The one to five carbon alkyl groups are preferred, especially the one and two carbon members.

The substituted phenyl groups are phenyl groups which bear one or two (preferably one) halo, lower alkyl or lower alkoxy substituents. The four common halogens are contemplated, preferably chlorine and bromine in that order. The lower alkyl substituents are of the type described above and the lower alkoxy groups are of the same type, e.g., methoxy, ethoxy, propoxy, isopropoxy, butoxy and the like. The $C_1$-$C_5$ and especially $C_1$-$C_2$ lower alkyl and lower alkoxy groups are preferred. Illustrative are o-, m- or p-chlorophenyl, o-, m- or p-bromophenyl, o-, m- or p-tolyl, o-, m- or p-methoxyphenyl, 3,5-dichlorophenyl, 2,4-dimethylphenyl, 2,6-dimethoxyphenyl and the like.

The symbols have the following meanings in formula I and throughout this specification.

The phenyl-lower alkyl groups are those in which a phenyl group is attached to a lower alkyl group of the type described above, e.g., phenylmethyl, phenylethyl and the like.

The di(lower alkyl)amino-lower alkyl groups include, for example, dimethylaminomethyl, dimethylaminoethyl, dimethylaminopropyl, diethylaminopropyl, (methyl)ethylaminoethyl, etc.

The dotted lines within the pyrimidine ring indicate that there is a single double bond in that ring attached to one or the other nitrogen, i.e., in either the 1,2-position or in the 2,3-position. The dotted lines attached to the $R^3$'s indicate that $R^3$ is linked to the nitrogen atom which is not double bonded. In other words, the double bond can be in the 1,2-position and $R^3$ is attached to the nitrogen in the 3-position in which case the compounds of the invention are 3,7-dihydro-4H-pyrazolo[4',3':5,6]-pyrido-[4,3-d]pyrimidin-4-ones which have the formula Preferred are those compounds of either formula Ia or formula Ib wherein $R^1$ is hydrogen or lower alkyl, especially lower alkyl and most especially ethyl; $R^2$, $R^4$ and $R^5$ each is hydrogen or lower alkyl, especially hydrogen; and $R^3$ is hydrogen, lower alkyl, especially $C_1$-$C_5$ lower alkyl, phenylmethyl or di(lower alkyl)amino-lower alkyl, especially dimethylaminoethyl or dimethylaminopropyl.

DETAILED DESCRIPTION

The new compounds of formula I are produced by reacting a 4-aminopyrazolo[3,4-b]pyridine-5-carboxamide with an acid having the formula

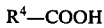
$R^4$—COOH (II)

or an alkyl orthoformate having the formula

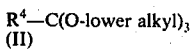
$R^4$—C(O-lower alkyl)$_3$
(II)

at an elevated temperature up to reflux temperature for a period up to about 48 hours.

When the acid or orthoformate ester is made to react with a 4-aminopyrazolo[3,4-b]pyridin-5-carboxamide in which the nitrogen in the 4-position is unsubstituted and the nitrogen in the 5-carboxamide group bears a substituent $R^3$(other than hydrogen), i.e., a compound having the formula

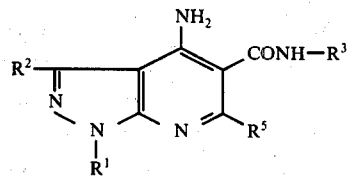
(IV)

then cyclization results in the formation of a 3,7-dihydro-4H-pyrazolo[4',3':5,6]pyrido[4,3-d]pyrimidin-4-one of formula Ia.

When, however, the starting material is a 4-aminopyrazolo[3,4-b]pyridin-5-carboxamide having an $R^3$ substituent (other than hydrogen) on the nitrogen in the 4-position and the amido nitrogen in the 5-position is unsubstituted, i.e., a compound having the formula

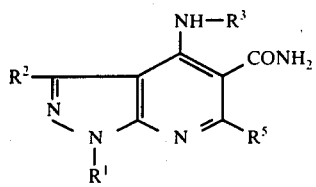

then cyclization results in the formation of a 1,7-dihydro-4H-pyrazolo[4',3':5,6]pyrido[4,3-d]pyrimidin-4-one of formula Ib.

When an unsubstituted starting material is used, i.e., $R^3$ in either formula IV or V is hydrogen, then an unsubstituted product of formula I is obtained.

The starting materials of formulas IV and V are produced as described in our U.S. Pat. Nos. 3,840,546, issued Oct. 8, 1974, and 3,966,746, issued June 29, 1976.

The new compounds of this invention have anti-inflammatory properties and are useful, for example, to reduce local inflammatory conditions such as those of an edematous nature or resulting from proliferation of connective tissue in various mammalian species such as rats, dogs and the like when given orally in dosages of about 5 to 75 mg./kg./day, preferably 10 to 50 mg./kg./day, in single or 2 to 4 divided doses, as indicated by the carageenan edema assay in rats. The active substance can be utilized in compositions such as tablets, capsules, solutions or suspensions containing up to about 500 mg. per unit of dosage of a compound of mixture of compounds of formula I. They are compounded in conventional manner with a physiologically acceptable vehicle or carrier, excipient, binder, preservative, stabilizer, flavor, etc. as called for by accepted pharmaceutical practice. Topical preparations containing about 0.05 to 5 percent by weight of active substance in a lotion or cream can also be used.

The new compounds of this invention, in addition, have central nervous system depressant activity and can be used as tranquilizers or ataractic agents for the relief of anxiety and tension states, for example, in mice, cats, dogs and other mammalian species. For this purpose a compound or mixture of compounds of formula I is administered orally or parenterally in a conventional dosage form such as tablet, capsule, injectable or the like. A single dose, or preferably 2 to 4 divided daily doses, provided on a basis of about 10 to 50 mg. per kilogram per day, preferably about 10 to 15 mg. per kilogram per day, is appropriate. These can be conventionally formulated in an oral or parenteral dosage form as described above.

The following examples are illustrative of the invention and constitute preferred embodiments as well as models for the preparation of additional members of the series. All temperatures are in degrees celsius.

EXAMPLE 1

7-Ethyl-1,7-dihydro-4H-pyrazolo[4',3':5,6]pyrido[4,3-d]-pyrimidin-4-one 20.6 g. of 4-amino-1-ethylpyrazolo[3,4-b]pyridine-5-carboxylic acid, (U.S. Pat. No. 3,833,594) are refluxed in 200 ml. of thionyl chloride with stirring for 12 hours. The excess of thionyl chloride is distilled off and the residue added to about 200 ml. of liquid ammonia. The mixture is stirred at room temperature until the ammonia is evaporated. The crystalline residue is treated with 100 ml. of water; crude 4-amino-1-ethylpyrazolo[3,4-b]-pyridin-5-carboxamide is filtered off and recrystallized from butanol, yield: 14.8 g. (72%); m.p. 261.0°.

20.5 g. of 4-amino-1-ethylpyrazolo[3,4-b]pyridin-5-carboxamide are refluxed with stirring for 24 hours with 100 ml. of triethyl orthoformate. The excess ester is removed in vacuo and the residue recrystallized from dimethylformamide to obtain 7-ethyl-1,7-dihydro-4H-pyrazolo[4',3':5,6]pyrido[4,3-d]pyrimidin-4-one, yield: 19 g. (88%); m.p. 320°–322°.

EXAMPLE 2

3,7-Diethyl-4H-pyrazolo[4',3':5,6]pyrido[4,3-d]pyrimidin-4-one 20.6 g. of 4-amino-1-ethylpyrazolo[3,4-b]pyridine-5-carboxylic acid is refluxed in 200 ml. of thionyl chloride with stirring for 12 hours. After evaporation of the excess thionyl chloride, the remaining acid chloride is suspended in 200 ml. of dry dioxane and treated with 40 ml. of ethylamine with cooling at 10° and stirring. The mixture is stirred for 12 hours at room temperature, evaporated to dryness in vacuo and about 150 ml. of water are added. 4-amino-1-ethylpyrazolo[3,4-b]pyridin-5-N-ethylcarboxamide is filtered off, dried in a desiccator and recrystallized from ethyl acetate, yield: 18 g. (17%); m.p. 140°–142°.

23.3 g. of 4-amino-1-ethylpyrazolo[3,4-b]-pyridin-5-N-ethylcarboxamide are refluxed for 48 hours with 100 ml. of triethyl orthoformate. The excess ester is removed in vacuo and the crystalline residue recrystallized from methanol to obtain 3,7-diethyl-4H-pyrazolo[4',3':5,6]-pyrido-[4,3-d]pyrimidin-4-one, yield: 17.5 g. (72%); m.p. 167°–169°.

Following the procedure of Example 2, but substituting for the 4-amino-1-ethylpyrazolo[3,4-b]pyrimidin-5-N-ethylcarboxamide the carboxamides listed below, the compounds of Examples 3–6 are obtained.

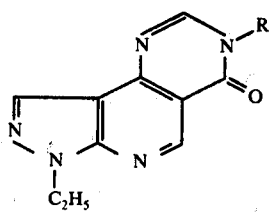

| Ex. | Carboxamide | R³ | m.p. | % Yield | Recrystallization solvent |
|---|---|---|---|---|---|
| 3 | 4-amino-1-ethylpyrazolo[3,4-b]pyridine-5-CONHCH(CH₃)C₂H₅ | —CH(CH₃)C₂H₅ | 110–112° | 87 | methanol |
| 4 | 4-amino-1-ethylpyrazolo[3,4-b]pyridine-5-CONHC₄H₉ | —(CH₂)₃CH₃ | 120–121° | 75 | butanol |
| 5 | 4-amino-1-ethylpyrazolo[3,4-b]pyridine-5-CONH(CH₂)₃N(CH₃)₂ | —(CH₂)₃N(CH₃)₂ | 90–92° | 71 | ethyl acetate |
| 6 | 4-amino-1-ethylpyrazolo[3,4-b]pyridine-5-CONH(CH₂)₂N(CH₃)₂ | —(CH₂)₂N(CH₃)₂ | 260–263° | 63 | ethyl acetate |

EXAMPLE 7

7-Ethyl-3,7-dihydro-3-(phenylmethyl)-4H-pyrazolo[4′,3′:5,6]-pyrido[4,3-d]pyrimidin-4-one 20.6 g. of 4-amino-1-ethylpyrazolo[3,4-b]pyridine-5-carboxylic acid are converted to the corresponding acid chloride as described in Example 1. This acid chloride is suspended in 200 ml. of dry benzene and treated with 30.2 g. of benzylamine. The mixture is stirred for 10 hours at room temperature and then filtered. The crystalline product, 4-amino-1-ethylpyrazolo[3,4-b]pyridin-5-N-(phenylmethyl)-carboxamide is washed with water and recrystallized from methanol, yield: 21 g. (71%); m.p. 212°–213°.

29.5 g. of 4-amino-1-ethylpyrazolo[3,4-b]pyridin-5-N-(phenylmethyl)carboxamide are refluxed with stirring in 150 ml. of formic acid for 24 hours. The acid is removed under reduced pressure and the crystalline residue recrystallized from butanol to obtain 7-ethyl-3,7-dihydro-3-(phenylmethyl)-4H-pyrazolo[4′,3′:5,6]-pyrido[4,3-d]pyrimidin-4-one, yield: 21 g. (69%); m.p. 198°–200°.

EXAMPLE 8

7-Ethyl-3,7-dihydro-3-(3-methylbutyl)-4H-pyrazolo[4′,3′:5,6]-pyrido[4,3-d]pyrimidin-4-one 20.6 g. of 4-amino-1-ethylpyrazolo[3,4-b]pyrimidine-5-carboxylic acid are converted to the acid chloride by treatment with thionyl chloride as described in Example 1, and the acid chloride obtained is treated with 3-methylbutylamine according to the procedure of Example 7 to obtain 4-amino-1-ethyl pyrazolo[3,4-b]pyridin-5-N-(3-methylbutyl)carboxamide, yield: 19 g. (65%); m.p. 218°–220° (ethyl acetate).

By substituting for the 4-amino-1-ethylpyrazolo-[3,4-b]pyridin-5-N-(phenylmethyl)carboxamide in the procedure of Example 7, 4-amino-1-ethylpyrazolo[3,4-b]pyridin-5-N-(3-methylbutyl)carboxamide, 7-ethyl-3,7-dihydro-3-(3-methylbutyl)-4H-pyrazolo[4′,3′:5,6]-pyrido[4,3-d]pyrimidin-4-one is obtained, yield: 78%; m.p. 165°–167° (ethanol).

EXAMPLE 9

7-Ethyl-1,7-dihydro-1-(1-methylethyl)-4H-pyrazolo[4′,3′:5,6]-pyrido[4,3-d]pyrimidin-4-one 27.6 g of 1-ethyl-4-(methylethyl)aminopyrazolo[3,4-b]-pyridine-5-carboxylic acid, ethyl ester [J. Het. Chem. 9, 235 (1972)] are refluxed for 5 hours in a solution of 10 g. of potassium hydroxide in 100 ml. of alcohol. After this time, the solvent is removed in vacuo and the residue is dissolved in 100 ml. of water and acidified with dilute hydrochloric acid. The precipitated 1-ethyl-4-(methylethyl)-aminopyrazolo[3,4-b]pyridine-5-carboxylic acid is filtered off (m.p. 193°–196°). This acid is refluxed in 100 ml. of thionyl chloride for 12 hours.

After evaporation of the excess thionyl chloride, the residue is added to about 200 ml. of liquid ammonia and allowed to stand at room temperature until the ammonia is evaporated. The crystalline residue is treated with 100 ml. of water and filtered. The product, 1-ethyl-4-(methylethyl)aminopyrazolo[3,4-b]pyridin-5-carboxamide, is recrystallized from alcohol, yield: (overall) 14.5 g. (59%); m.p. 169°–170°.

24.7 g. of 1-ethyl-4-(methylethyl)aminopyrazolo-[3,4-b]pyridin-5-carboxamide are reacted with 100 ml. of triethyl orthoformate at reflux temperature for 24 hours with stirring. After the ester is removed, the remaining 7-ethyl-1,7-dihydro-1-(1-methylethyl)-4H-pyrazolo[4′,3′:5,6]-pyrido[4,3-d]pyrimidin-4-one is recrystallized from ethanol, yield: 23 g. (89%); m.p. 260°–263°.

Following the procedure of Example 9, but substituting for the 1-ethyl-4-(methylethyl)aminopyrazolo[3,4-b]pyridin-5-carboxamide the carboxamide listed below, the following compounds are obtained:

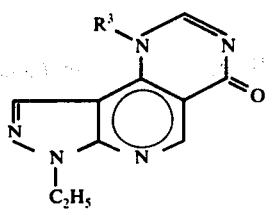

| Ex. | $R^1$ | $R^2$ | $R^3$ | $R^4$ | $R^5$ |
|---|---|---|---|---|---|
| 13 | H | | $CH_3$ | H | $CH_3$ | H |
| 14 | H | | H | H | H | H |
| 15 | $C_3H_7$ | | H | $C_4H_9$ | H | H |
| 16 | $C_2H_5$ | | H | | H | $CH_3$ |
| 17 | $CH_3$ | | $CH_3$ | $-CH_2N(CH_3)_2$ | $CH_3$ | H |
| 18 | $C_2H_5$ | | H | $C_4H_9$ | $C_2H_5$ | $C_2H_5$ |
| 19 | $C_2H_5$ | | H | | H | $CH_3$ |

| Ex. | Carboxamide | $R^3$ | m.p. | Yield % | Recrystallization solvent |
|---|---|---|---|---|---|
| 10 | HN(CH$_2$)$_2$CH(CH$_3$)$_2$ carboxamide | $-(CH_2)_2CH(CH_3)_2$ | 223–225° | 68 | ethyl acetate |
| 11 | HNC$_4$H$_9$ carboxamide | $-C_4H_9$ | 218.6° | 71 | ethanol |
| 12 | HN(CH$_2$)$_2$N(CH$_3$)$_2$ carboxamide | $-(CH_2)_2N(CH_3)_2$ | 204.8° | 58 | ethyl acetate |

Following the procedure of Example 2, but substituting for the 4-amino-1-ethylpyrazolo[3,4-b]pyridin-5-N-ethylcarboxamide the carboxamide having the substituents $R^1$, $R^2$, $R^3$ and $R^5$ below and substituting for the triethyl orthoformate the orthoformate $R^4$—C(OC$_2$H$_5$)$_3$ with the $R^4$ shown below, the product of the following formula is obtained:

| 20 | $C_2H_5$ | $C_2H_5$ | (4-OCH$_3$-phenyl) | H | H |
| 21 | $C_2H_5$ | H | (4-Cl-phenyl) Br | H | $CH_3$ |

(2-bromophenyl)

-continued

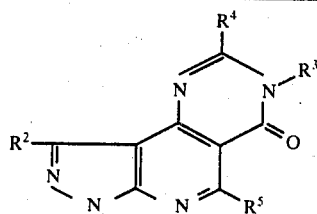

| Ex. | R¹ | R² | R³ | R⁴ | R⁵ |
|---|---|---|---|---|---|
| 22 | C₂H₅ | CH₃ | —⟨phenyl⟩—CH₃ (p-tolyl) | H | H |
| 23 | H | H | —⟨2,5-dichlorophenyl⟩ | CH₃ | CH₃ |
| 24 | C₂H₅ | H | —CH₂—⟨phenyl⟩ | H | H |
| 25 | ⟨cyclohexyl/phenyl⟩ | H | C₄H₉ | H | H |
| 26 | H | H | —(CH₂)₂N(C₂H₅)₂ | CH₃ | H |
| 27 | C₂H₅ | CH₃ | —(CH₂)₃N(CH₃)₂ | H | CH₃ |

Following the procedure of Example 9, but substituting for 1-ethyl-4-(methylethyl)aminopyrazolo[3,4-b]pyridin-5-carboxamide the carboxamide having the substituents R¹, R², R³ and R⁵ below and substituting for the triethyl orthoformate the orthoformate R⁴—C-(OC₂H₅)₃ with the R⁴ shown below, the product of the following formula with the substituents indicated, is obtained:

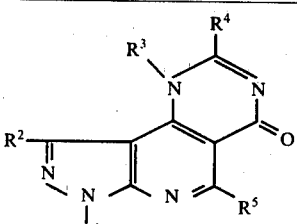

| Ex. | R¹ | R² | R³ | R⁴ | R⁵ |
|---|---|---|---|---|---|
| 28 | C₂H₅ | CH₃ | —CH₂—⟨phenyl⟩ | H | CH₃ |
| 29 | C₂H₅ | CH₃ | —(CH₂)₃N(CH₃)₂ | H | CH₃ |
| 30 | H | H | —(CH₂)₂N(C₂H₅)₂ | CH₃ | H |
| 31 | C₂H₅ | H | —(CH₂)₂—⟨phenyl⟩ | H | H |
| 32 | C₂H₅ | C₂H₅ | —⟨phenyl-Cl⟩ | H | H |
| 33 | C₂H₅ | H | C₄H₉ | C₂H₅ | C₂H₅ |
| 34 | C₂H₅ | H | —⟨phenyl⟩ | H | CH₃ |
| 35 | H | H | H | H | H |
| 36 | H | CH₃ | H | CH₃ | H |
| 37 | C₃H₇ | H | C₄H₉ | H | H |
| 38 | CH₃ | CH₃ | —CH₂N(CH₃)₂ | CH₃ | H |

-continued

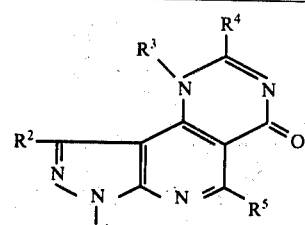

| Ex. | R¹ | R² | R³ | R⁴ | R⁵ |
|---|---|---|---|---|---|
| 39 | C₂H₅ | H | —⟨phenyl⟩—OCH₃ | H | CH₃ |
| 40 | C₂H₅ | H | —⟨phenyl⟩—Br | H | CH₃ |
| 41 | C₂H₅ | CH₃ | —⟨phenyl⟩—CH₃ | H | H |
| 42 | H | H | —⟨2,5-dichlorophenyl⟩ | CH₃ | CH₃ |
| 43 | ⟨phenyl⟩ | H | C₄H₉ | H | H |
| 44 | ⟨phenyl⟩ | H | —(CH₂)₂N(CH₃)₂ | H | H |

What is claimed is:

1. A compound of the formula

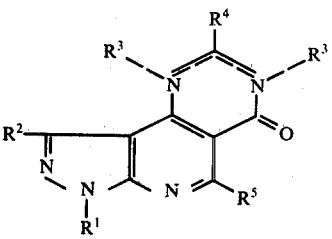

wherein
R¹ is hydrogen, lower alkyl or phenyl;
R², R⁴ and R⁵ each is hydrogen or lower alkyl; and
R³ is hydrogen, lower alkyl, phenyl, substituted phenyl wherein the phenyl substituent is one or two halo, lower alkyl or lower alkoxy groups, phenyl-lower alkyl or di(lower alkyl)amino-lower alkyl.

2. A compound of the formula

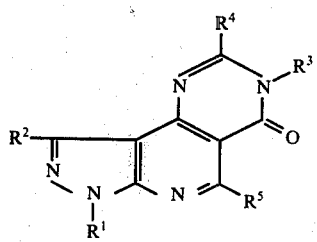

wherein R¹, R², R³, R⁴ and R⁵ have the same meaning as in claim 1.

3. A compound of the formula

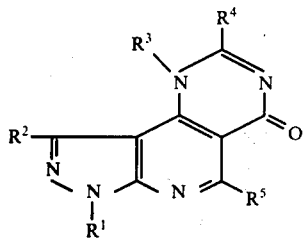

wherein $R^1$, $R^2$, $R^3$, $R^4$ and $R^5$ have the same meaning as in claim 1.

4. A compound as in claim 1 wherein $R^1$, $R^2$, $R^4$ and $R^5$ each is hydrogen or lower alkyl; and $R^3$ is hydrogen, lower alkyl or di(lower alkyl)amino-lower alkyl.

5. A compound as in claim 3 wherein $R^1$, $R^2$, $R^4$ and $R^5$ each is hydrogen or lower alkyl; and $R^3$ is hydrogen, lower alkyl or di(lower alkyl)amino-lower alkyl.

6. A compound as in claim 2 wherein $R^3$ is lower alkyl.

7. A compound as in claim 3 wherein $R^3$ is lower alkyl.

8. A compound as in claim 2 wherein $R^3$ is di(lower alkyl)amino-lower alkyl.

9. A compound as in claim 3 wherein $R^3$ is di(lower alkyl)amino-lower alkyl.

10. A compound as in claim 1 wherein $R^1$ is lower alkyl and $R^2$, $R^4$ and $R^5$ each is hydrogen.

11. A compound as in claim 2 wherein $R^1$ is lower alkyl; $R^2$, $R^4$ and $R^5$ each is hydrogen; and $R^3$ is lower alkyl.

12. A compound as in claim 2 wherein $R^1$ is lower alkyl; $R^2$, $R^4$ and $R^5$ each is hydrogen; and $R^3$ is di(lower alkyl)amino-lower alkyl.

13. A compound as in claim 3 wherein $R^1$ is lower alkyl; $R^2$, $R^4$ and $R^5$ each is hydrogen; and $R^3$ is lower alkyl.

14. A compound as in claim 3 wherein $R^1$ is lower alkyl; $R^2$, $R^4$ and $R^5$ each is hydrogen; and $R^3$ is di(lower alkyl)amino-lower alkyl.

15. A compound as in claim 2 wherein $R^1$ is ethyl; and $R^2$, $R^3$, $R^4$ and $R^5$ each is hydrogen.

16. A compound as in claim 2 wherein $R^1$ is ethyl; $R^2$, $R^4$ and $R^5$ each is hydrogen; and $R^3$ is ethyl.

17. A compound as in claim 2 wherein $R^1$ is ethyl; $R^2$, $R^4$ and $R^5$ each is hydrogen; and $R^3$ is dimethylaminopropyl.

18. A compound as in claim 3 wherein $R^1$ is ethyl; $R^2$, $R^4$ and $R^5$ each is hydrogen; and $R^3$ is 1-methylethyl.

19. A compound as in claim 3 wherein $R^1$ is ethyl; $R^2$, $R^4$ and $R^5$ each is hydrogen; and $R^3$ is dimethylaminoethyl.

* * * * *